US010761226B2

(12) United States Patent
Choi

(10) Patent No.: US 10,761,226 B2
(45) Date of Patent: Sep. 1, 2020

(54) HANDLE FOR RADIATION DETECTOR

(71) Applicant: Vieworks Co., Ltd., Anyang-si, Gyeonggi-do (KR)

(72) Inventor: Jung Min Choi, Ansan-si (KR)

(73) Assignee: VIEWORKS CO., LTD., Anyang-si, Gyeonggi-do (KR)

( * ) Notice: Subject to any disclaimer, the term of this patent is extended or adjusted under 35 U.S.C. 154(b) by 0 days.

(21) Appl. No.: 16/293,593

(22) Filed: Mar. 5, 2019

(65) Prior Publication Data
US 2019/0277985 A1    Sep. 12, 2019

(30) Foreign Application Priority Data

Mar. 6, 2018   (KR) .................. 10-2018-0026247

(51) Int. Cl.
*A61B 6/00*    (2006.01)
*G01T 7/00*    (2006.01)

(52) U.S. Cl.
CPC ..................... *G01T 7/00* (2013.01)

(58) Field of Classification Search
CPC ........... A61B 6/00; A61B 6/4283; G01T 1/29; G01T 7/00; G03B 42/04
See application file for complete search history.

(56) References Cited

U.S. PATENT DOCUMENTS

| 7,396,158 | B2 | 7/2008 | Grosse |
| 2006/0256928 | A1 | 11/2006 | Grosse |
| 2008/0240358 | A1 | 10/2008 | Utschig et al. |
| 2010/0038549 | A1* | 2/2010 | Nishino ............... G03B 42/04 250/370.09 |
| 2010/0054399 | A1* | 3/2010 | Nishino ............... A61B 6/4233 378/28 |
| 2012/0280601 | A1* | 11/2012 | Watanabe ........... G03B 42/04 312/223.1 |
| 2013/0051531 | A1* | 2/2013 | Kobayashi ......... A61B 6/4233 378/98 |

FOREIGN PATENT DOCUMENTS

| EP | 2380495 A1 | 10/2011 |
| JP | 2008-256685 A | 10/2008 |
| JP | 4717272 B2 | 7/2011 |
| JP | 2013-024995 A | 2/2013 |
| JP | 5288896 B2 | 9/2013 |
| KR | 101502844 B1 | 3/2015 |

OTHER PUBLICATIONS

Korean Office Action dated Feb. 27, 2019.

* cited by examiner

*Primary Examiner* — Mark R Gaworecki
(74) *Attorney, Agent, or Firm* — Rabin & Berdo, P.C.

(57) ABSTRACT

The present invention relates to a handle for a radiation detector including a body grasped by a user, a first hook coupled to a coupling groove formed on a radiation detector body, a button member moving according to the user's manipulation in such a manner as to release a coupling state of the handle, a second hook engaging with the button member in such a manner as to be coupled to a coupling groove formed on the radiation detector body, and a double locking part disposed inside the body, whereby the handle can be detachably coupled to the radiation detector body, irrespective of its attaching direction, and the radiation detector can be rapidly and conveniently carried by the user.

9 Claims, 13 Drawing Sheets

HANDLE FOR RADIATION DETECTOR

BACKGROUND OF THE INVENTION

Field of the Invention

The present invention relates to a handle for a radiation detector that is detachably mounted on a radiation detector body, and more particularly, to a handle for a radiation detector that is capable of being detachably coupled to a radiation detector body, irrespective of its attaching direction, thereby allowing a radiation detector to be rapidly and stably carried by a user.

Background of the Related Art

Radiation means alpha ($\alpha$) rays, beta ($\beta$) rays, gamma ($\gamma$) rays, and x rays emitted during a radioactive element having an unstable atomic nucleus is decayed, and since the radiation does not have any color, sound, taste, smell, and feeling, it cannot be detected through a human's sensory organs. So as to detect the radiation, accordingly, a radiation detector has to be used.

In conventional practices, the x rays are transmitted to an object, and next, an amount of x rays attenuated is analyzed under a phenomenon where the x rays are attenuated according to a material, density, and thickness of the object, thereby obtaining images for the inside structures of the human body (for example, chest, abdomen, pelvis, skull, and so on). Accordingly, the radiation is generally used for disease diagnosis in a medical field. In addition to the medical field, however, the radiation has been recently utilized in various fields such as fields of industry and security, material science, universe physics, air/water pollution monitoring, etc.

As the fields utilizing the radiation are enlargedly varied, imaging places using the radiation, which are limited in indoors in the conventional practices, have been enlarged to outdoors, and also, imaging objects are varied from the human body to various kinds of materials, thereby making it necessary to need a portable radiation detector.

As shown in FIG. 1, a handle 100 is attached to an x-ray detector 10 as a kind of a radiation detector, and as the handle 100 is grasped by a user, the x-ray detector 10 can be easily carried. According to the conventional radiation detector, however, a direction where the handle 100 and the x-ray detector 10 are coupled to each other is determined in one (single) way, and accordingly, the handle 100 has to be adjusted to correspond to the direction coupled to the x-ray detector 10, thereby making it hard to rapidly couple the handle 100 to the x-ray detector 10.

In the conventional practice, moreover, the handle 100 is slidingly coupled to '⌊'-shaped grooves 11 formed on the x-ray detector 10, and accordingly, the handle 100 is coupled only in one way, thereby failing to achieve fast detachable coupling between the handle 100 and the x-ray detector 10 and causing a gap between the handle 100 and the x-ray detector 10 to make stability in their coupling undesirably lowered. While the x-ray detector 10 is being carried, accordingly, the handle 100 may be separated from the x-ray detector 10, so that the x-ray detector 10 may fall down to the ground, and in this case, it may be even damaged.

Such tries to improve the portability of the conventional radiation detectors fail to ensure stability in coupling between the handle and the radiation detector body, and therefore, there is a definite need for a new device capable of solving such problems.

SUMMARY OF THE INVENTION

Accordingly, the present invention has been made in view of the above-mentioned problems occurring in the related art, and it is an object of the present invention to provide a handle for a radiation detector that is capable of being detachably coupled to a radiation detector body, irrespective of its attaching direction, thereby ensuring conveniences in the coupling between the handle and the radiation detector body and achieving fast attachment of the handle to the radiation detector body in an emergency situation like explosive inspection.

It is another object of the present invention to provide a handle for a radiation detector that is configured to adopt hook coupling, not sliding coupling, thereby minimizing a gap between a radiation detector body and the handle to enhance stability in their coupling.

It is yet another object of the present invention to provide a handle for a radiation detector that is configured to have a double locking part composed of a trigger, a moving member, and a stopper, thereby preventing separation from a radiation detector body, while the radiation detector grasped by a user is being carried.

The technical problems to be achieved through the present invention are not limited as mentioned above, and other technical problems not mentioned herein will be obviously understood by one of ordinary skill in the art through the following description.

To accomplish the above-mentioned objects, according to one aspect of the present invention, there is provided a handle for a radiation detector, which is detachably mounted on a radiation detector body, the handle including: a body grasped by a user; a first hook coupled to a coupling groove formed on the radiation detector body; a button member moving according to the user's manipulation in such a manner as to release a coupling state of the handle; a second hook engaging with the button member in such a manner as to be coupled to a coupling groove formed on the radiation detector body; and a double locking part disposed inside the body.

According to the present invention, desirably, the double locking part includes: a trigger moving vertically according to a contact with the radiation detector body; a moving member connected to the body and moving forward in a direction of the trigger if the trigger moves vertically; and a stopper coupled to the moving member in such a manner as to prevent the moving member from moving forward if the handle is detached from the radiation detector body.

According to the present invention, desirably, the trigger includes: a curved surface portion adapted to allow the stopper to be bent according to the horizontal movement of the moving member; a locking groove adapted to fix the stopper thereto; and a protrusion portion whose one surface comes into contact with the moving member to prevent the forward movement of the moving member.

According to the present invention, desirably, the moving member further includes a manipulator exposed on the outer surface of the body in such a manner as to move the moving member forward or backward by the user's manipulation.

According to the present invention, desirably, if the first hook and the second hook are coupled to the coupling grooves of the radiation detector body, the trigger is ascended, so that the moving member moves forward to prevent the button member from being pressed.

According to the present invention, desirably, if the moving member moves backward to release the coupling state between the handle and the radiation detector body, the stopper is locked on the locking groove to prevent the moving member from moving forward.

According to the present invention, desirably, as the moving member moves backward, the button member can be pressed.

According to the present invention, desirably, if the button member is pressed in the state where the handle is coupled to the radiation detector body, a coupling state between the second hook and the coupling groove of the radiation detector body is released to allow one side of the handle to be separated from the radiation detector body, and the trigger is descended, so that the stopper escapes from the locking groove to allow the moving member to move forward until comes into contact with the protrusion portion.

To accomplish the above-mentioned objects, according to the other aspect of the present invention, there is provided a radiation detector including: a radiation detector body having a plurality of coupling grooves formed on at least one or more surfaces thereof; and a handle detachably coupled to the plurality of coupling grooves, wherein the handle includes: a body grasped by a user; a first hook coupled to one side coupling groove; a button member moving vertically according to the user's manipulation in such a manner as to release a coupling state of the handle; a second hook engaging with the button member and coupled to the other side coupling groove; and a double locking part having a trigger disposed at the inside of the body and moving vertically according to a contact with the radiation detector body, a moving member connected to the body by means of a spring and moving forward in a direction of the trigger if the trigger moves vertically, and a stopper coupled to the moving member in such a manner as to prevent the moving member from moving forward if the handle is detached from the radiation detector body.

According to the present invention, desirably, the plurality of coupling grooves are formed symmetrically on at least one or more surfaces of the radiation detector body.

BRIEF DESCRIPTION OF THE DRAWINGS

The above and other objects, features and advantages of the present invention will be apparent from the following detailed description of one of the embodiments of the invention in conjunction with the accompanying drawings, in which.

DETAILED DESCRIPTION OF THE INVENTION

Figure 1:
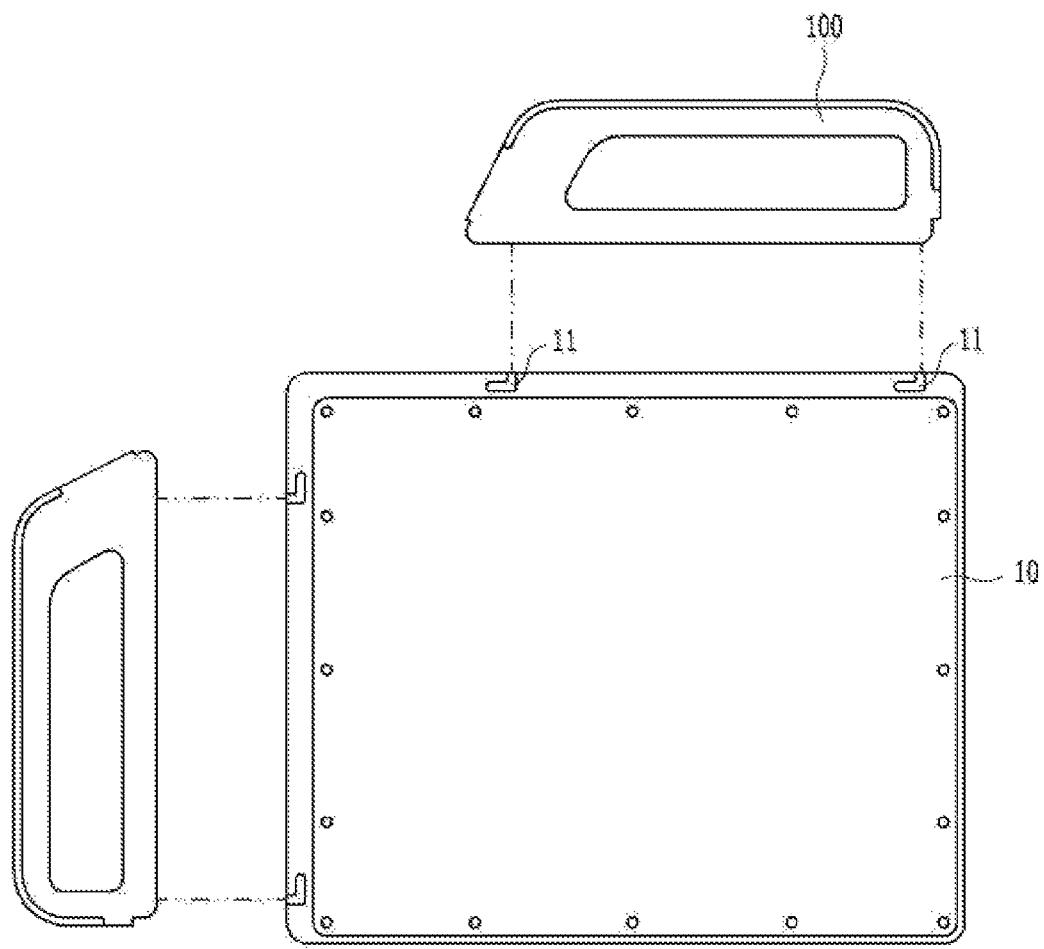
FIG. 1 is a front view showing a process wherein a handle from which coupling protrusions are formed is detachably mounted on a radiation detector body having '[ '-shaped coupling grooves in a conventional practice.

Hereinafter, the present invention is disclosed with reference to the attached drawings wherein the corresponding parts in the embodiments of the present invention are indicated by corresponding reference numerals and the repeated explanation on the corresponding parts will be avoided. If it is determined that the detailed explanation on the well known technology related to the present invention makes the scope of the present invention not clear, the explanation will be avoided for the brevity of the description.

When it is said that one element is described as being "connected" or "coupled" to the other element, one element may be directly connected or coupled to the other element, but it should be understood that another element may be present between the two elements. In the description, when it is said that one member is located "above" another member, it means that one member may come into contact with another member as well as yet another member may exist between the two members.

In this application, terms, such as "comprise", "include", or "have", are intended to designate those characteristics, numbers, steps, operations, elements, or parts which are described in the specification, or any combination of them that exist, and it should be understood that they do not preclude the possibility of the existence or possible addition of one or more additional characteristics, numbers, steps, operations, elements, or parts, or combinations thereof.

First, an explanation on a handle for a radiation detector according to the present invention will be given in detail with reference to FIGS. 2 and 3.

Figure 2:
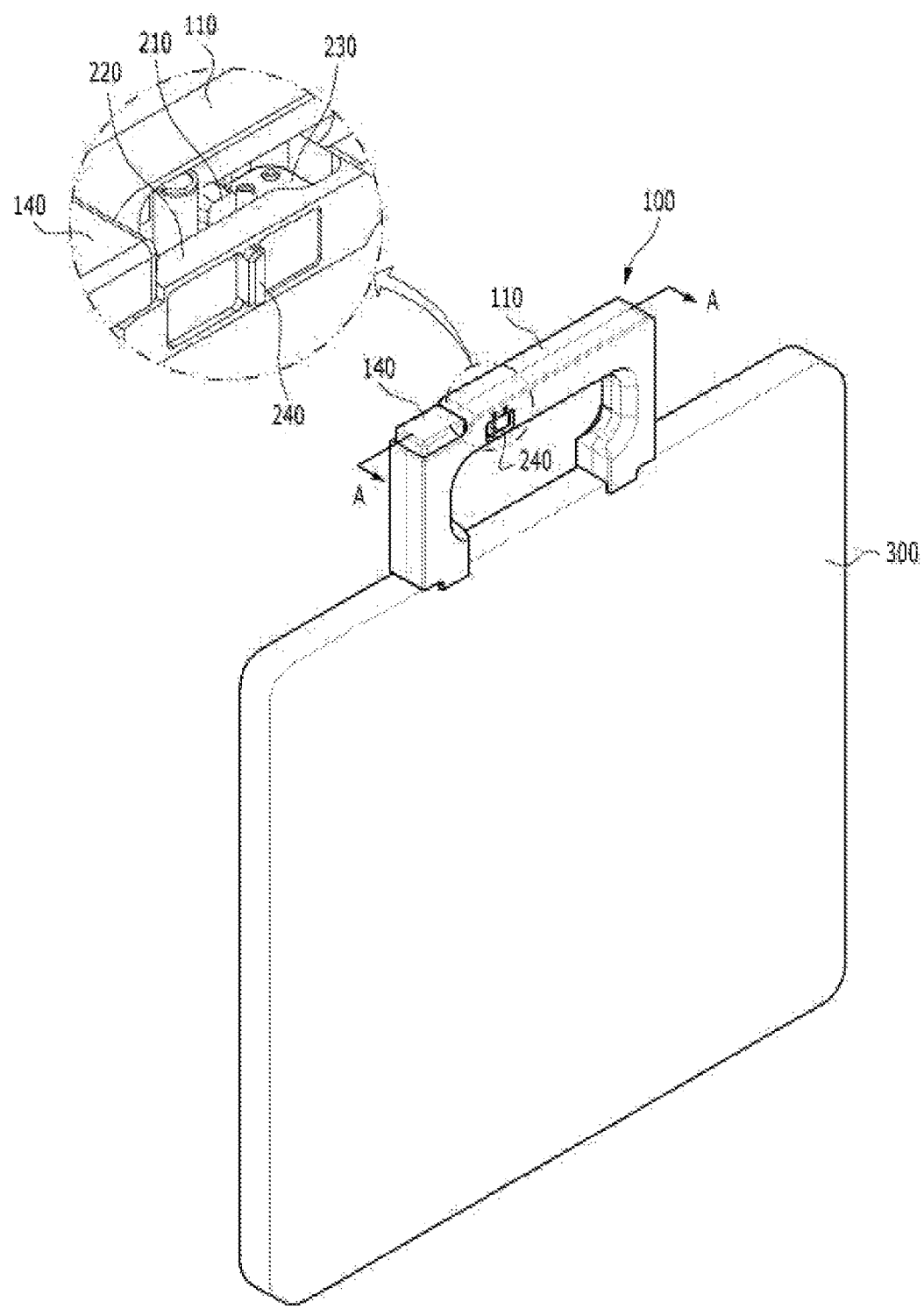
FIG. 2 is a perspective view showing a state where a handle for a radiation detector according to the present invention is attached to a radiation detector body.
Figure 3:
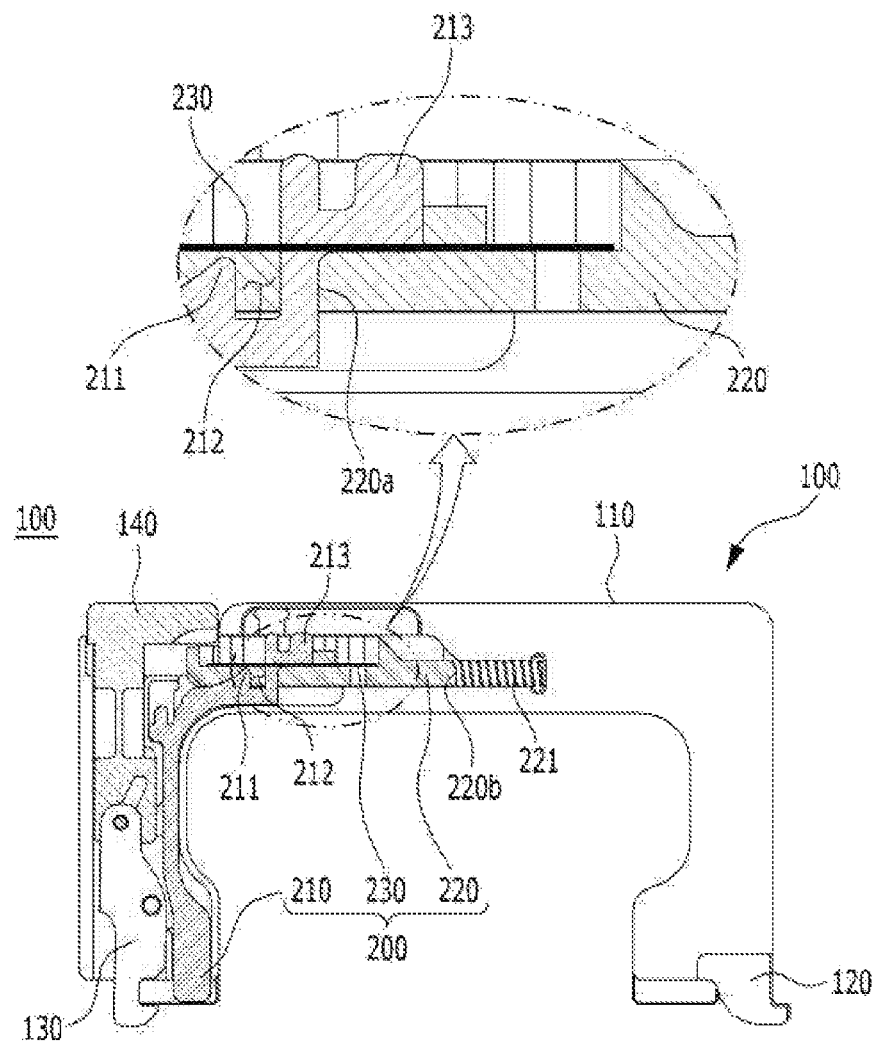
FIG. 3 is a sectional view taken along the line A-A of FIG. 2.

FIG. 2 is a perspective view showing a state where a handle for a radiation detector according to the present invention is attached to a radiation detector body, and FIG. 3 is a sectional view taken along the line A-A of FIG. 2.

According to the present invention, a handle 100 for a radiation detector, which is detachably mounted on a radiation detector body 300, includes: a body 110 grasped by a user in such a manner as to stably carry the radiation detector body 300; a first hook 120 disposed on one side lower end of the body 110 in such a manner as to be coupled to a coupling groove 310a formed on the radiation detector body 300; a button member 140 moving vertically with respect to a contacted surface between the handle 100 and the radiation detector body 300 according to the user's manipulation, that is, the user's pressing in such a manner as to release a coupling state of the handle 100; a second hook 130 coupled to the lower end of the button member 140 in such a manner as to rotate engagingly with the vertical movement of the button member 140, the second hook 130 being coupled to the other coupling groove 310b formed on the radiation detector body 300; and a double locking part 200 disposed inside the body 110 to prevent the button member 140 from being pressed in the state where the handle 100 is coupled to the radiation detector body 300.

In detail, the handle 100 is coupled to the radiation detector body 300 in such a manner as to couple the first hook 120 and the second hook 130 to the coupling grooves 310a and 310b formed on the radiation detector body 300, and next, the double locking part 200 serves to prevent the button member 140 from being pressed to prevent the coupling states between the first hook 120 and the second hook 130 and the coupling grooves 310a and Slob from being released, thereby more enhancing stability in their coupling when compared with the conventional radiation detector using the sliding coupling.

In the description and attached drawings, at this time, the button member 140 is located on top end surface of the handle 100 in such a manner as to move vertically according to the user's manipulation, and the second hook 130 rotates engagingly with the vertical movement of the button member 140 in such a manner as to be detachably coupled to the coupling groove of the radiation detector body 300, which are just exemplary.

Even though not shown in the drawings, the button member 140 may be located on a left or right side of the handle 100 in such a manner as to move horizontally (in a direction of the inside of the handle 100) by means of the user's manipulation, and the second hook 130 rotates engagingly with the horizontal movement of the button member 140 in such a manner as to be coupled to or decoupled from the coupling groove of the radiation detector body 300.

Otherwise, the button member 140 and the second hook 130 may be formed unitarily with each other, so that the second hook 130 is coupled to or decoupled from the coupling groove of the radiation detector body 300 by means of the user's manipulation of the button member 140.

Moreover, even if the button member 140 is located on the left or right side of the handle 100, not on the top end surface thereof, double locking through the double locking part 200 is carried out in the same manner as above.

Now, an explanation on the double locking part 200 will be given with reference to FIG. 3, and the double locking part 200 includes: a trigger 210 disposed at an adjacent area to the second hook 130 in such a manner as to move vertically with respect to a contacted surface with the radiation detector body 300 if the second hook 130 is coupled to the coupling groove 310b of the radiation detector body 300; a moving member 220 whose rear end 220b is connected to the inside of the body 110 by means of a spring 221 and moving forward (horizontally) in the direction of the trigger 210 by means of an elastic force of the spring 221 if the trigger 210 moves vertically; and a stopper 230 made of an elastic material and coupled to the moving member 220 in such a manner as to prevent the moving member 220 from moving forward if the handle 100 is detached from the radiation detector body 300.

At this time, the trigger 210 includes: a curved surface portion 211 whose surface is curvedly formed to allow the stopper 230 to be bent upward according to the forward and backward movements of the moving member 220; a locking groove 212 formed at an adjacent position to the curved surface portion 211 to fix the stopper 230 thereto if the handle 100 is detached from the radiation detector body 300; and a protrusion portion 213 whose one surface comes into contact with a contact surface 220a of the moving member 220 to prevent the forward movement of the moving member 220, and accordingly, the trigger 210 restricts the movements of the moving member 220 and the stopper 230 coupled to the moving member 220 according to the contact with the radiation detector body 300.

Furthermore, as mentioned above, the moving member 220 has the rear end 220b connected to the inside of the body 110 by means of the spring 221, so that it moves forward in the direction of the trigger 210 by means of the elastic force of the spring 221 to prevent the button member 140 from being pressed, thereby keeping the handle 100 from being separated from the radiation detector body 300 due to unintentional pressing of the button member 140. Contrarily, the moving member 220 moves backward by means of the user's manipulation to allow the user to press the button member 140, thereby making the handle 100 separated from the radiation detector body 300.

In detail, the moving member 220 is connected to the second hook 130 through the forward or backward horizontal movement thereof to control the movement of the button member 140 adjusting the movement of the second hook 130, thereby preventing the handle 100 from being separated from the radiation detector body 300 or releasing the double locking between the handle 100 and the radiation detector body 300.

At this time, as shown in FIG. 2, the moving member 220 further includes a manipulator 240 exposed on the outer surface of the body 110 in such a manner as to move forward or backward by the user to allow the moving member 220 to move forward or backward. For example, if the manipulator 240 is manipulated (pushed) backward with respect to the button member 140 by the user, the moving member 220 moves backward to compress the spring 221 connected to the rear end 220b thereof.

Next, the stopper 230, which is made of the elastic material and is coupled to the moving member 220, moves along the curved surface portion 211 of the trigger 210 according to the forward or backward movement of the moving member 220 in the process where the handle 100 is detachably coupled to the radiation detector body 300, so that it is bent upward or locked onto the locking groove 212 to prevent the moving member 220 from moving forward.

At this time, as shown in FIG. 3, the stopper 230 is coupled to the inside of the moving member 220, but of course, the stopper 230 may be coupled to the outside of the moving member 220, without being limited thereto.

Moreover, as shown in FIG. 3, the trigger 210 is coupled to the inside of the moving member 220, but of course, the moving member 220 may be coupled to the inside of the trigger 210, without being limited thereto.

Next, an explanation on a process of coupling the handle 100 according to the present invention to the radiation detector body 300 will be in detail given with reference to FIGS. 4A to 4D.

Figure 4A:
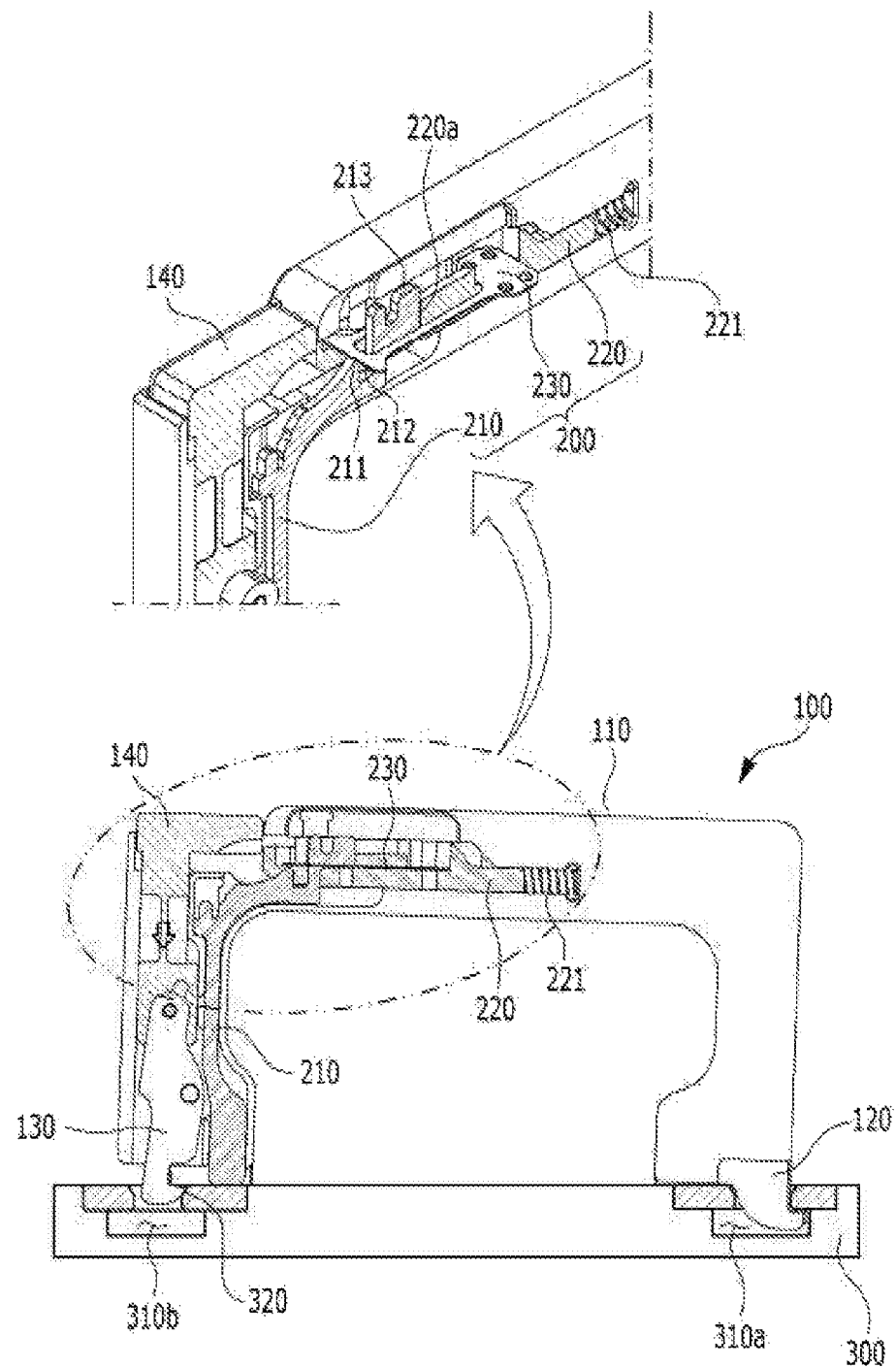
FIGS. 4A to 4D are sectional views showing a process wherein the handle according to the present invention is coupled to the radiation detector body.
Figure 4B:
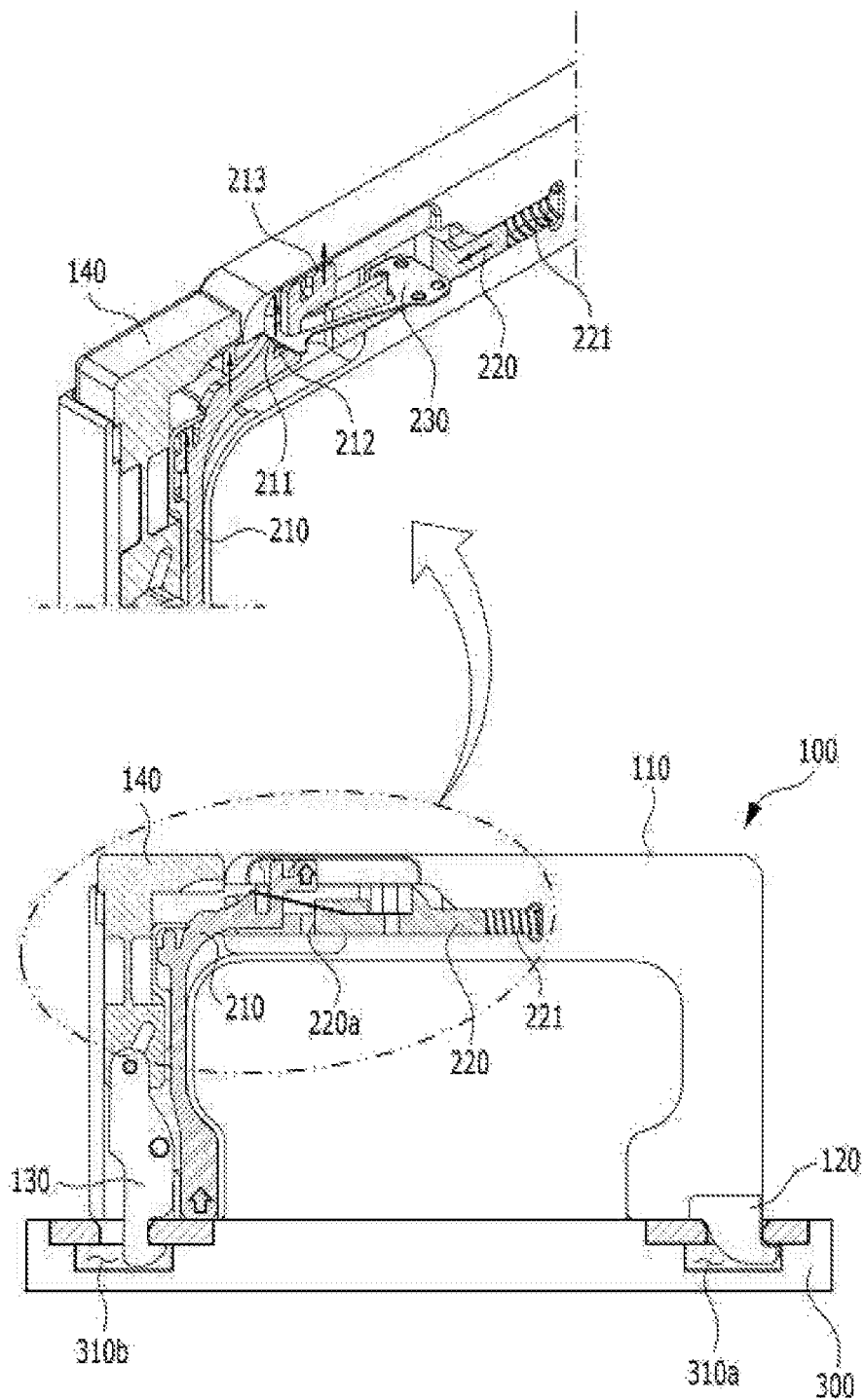
Figure 4C:
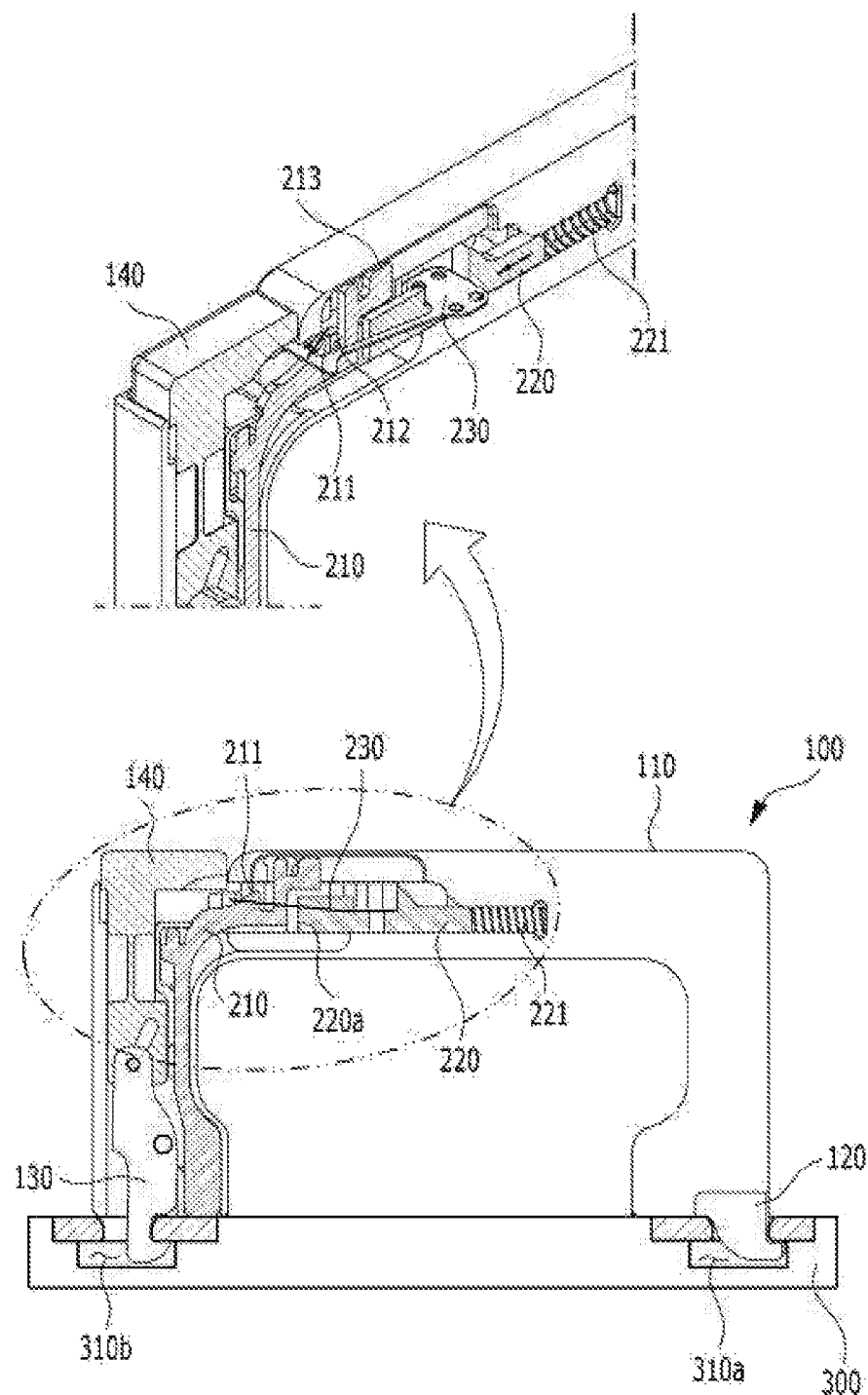
Figure 4D:
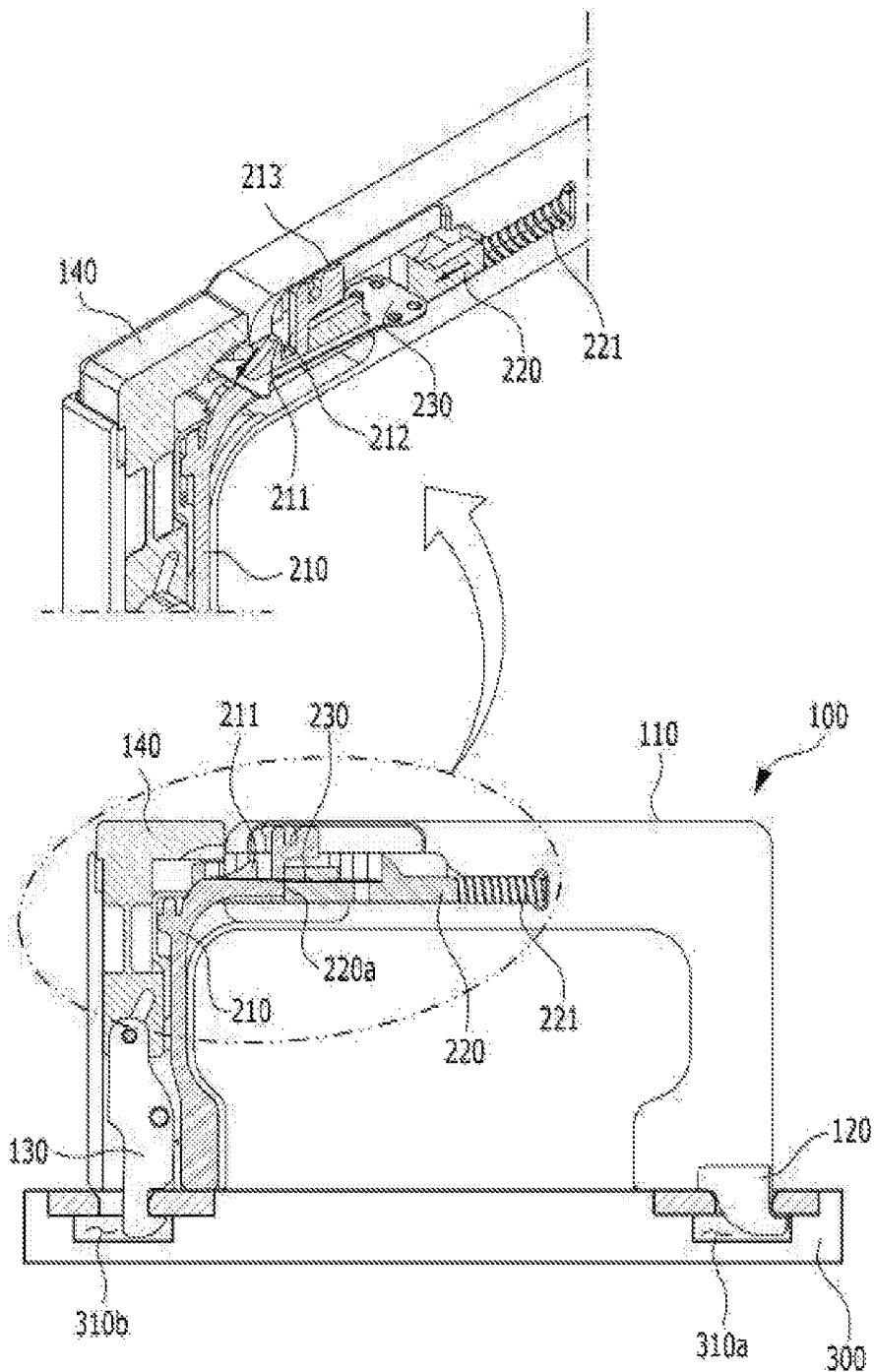

At this time, FIG. 4A is a sectional view showing a process wherein the second hook 130 is coupled to the other coupling groove 310b in a state where the first hook 120 is coupled to one coupling groove 310a, FIG. 4B is a sectional view showing a process wherein the trigger 210 coming into contact with the radiation detector body 300 is ascended, FIG. 4C is a sectional view showing a process wherein the moving member 220 moves forward after the trigger 210 is completely ascended, and FIG. 4D is a sectional view showing a state wherein the moving member 220 moves forward to allow the contact surface 220a to come into contact with one surface (the underside of the protrusion portion 213) of the trigger 210.

Further, as shown in FIGS. 4A to 4D, the first hook 120 is coupled to the coupling groove 310a formed at the right side, and the second hook 130 is coupled to the coupling groove 310b formed at the left side, which is just exemplary. Accordingly, the first hook 120 may be coupled to the coupling groove 310b formed at the left side, and the second hook 130 may be coupled to the coupling groove 310a formed at the right side.

According to the present invention, the first hook 120 is coupled to the coupling groove 310a or 310b, and the second hook 130 is coupled to the other coupling groove 310b or 310a, so that the handle 100 is coupled to the radiation detector body 300. In detail, as shown in FIG. 4A, if the handle 100 is inclined in the opposite direction to the first hook 120 in the state where the first hook 120 is coupled to the coupling groove 310a, the lower end portion of the second hook 130 comes into contact with a slant surface 320 of the coupling groove 310b and thus rotates in a direction of the outside of the slant surface 320 (in a clockwise direction in FIG. 4A), and also, the button member 140 connected to the second hook 130 is descended by a given height.

After that, if the handle 100 is completely inclined to come into close contact with the radiation detector body 300, the radiation detector body 300 is brought into contact with the underside of the trigger 210, and accordingly, the trigger 210 is ascended, as shown in FIG. 4B, so that the stopper 230 located on top end of the curved surface portion 211 of the trigger 210 becomes bent upward.

Like this, if the trigger 210 is ascended, the protrusion portion 213 of the trigger 210 is also ascended, and as shown in FIG. 4C, the moving member 220 compressed by means of the protrusion portion 213 moves forward by means of the elastic force of the spring 221, so that the stopper 230 coupled to the moving member 220 also moves forward along the curved surface portion 211.

If the moving member 220 moves forward until comes into contact with one surface of the trigger 210, as shown in FIG. 4D, the front end of the moving member 220 is located on the underside of the button member 140, thereby preventing the button member 140 from being pressed.

In detail, the front end of the moving member 220 is located on the underside of the button member 140, thereby achieving double locking for the handle 100, so that the handle 100 is not separated from the radiation detector body 300 even if the button member 140 is unintentionally pressed in a process where the handle 100 is grasped by the user.

Next, an explanation on a process of releasing the coupling state between the handle 100 and the radiation detector body 300, that is, separating the handle 100 from the radiation detector body 300, will be in detail given with reference to FIGS. 5A to 5D.

Figure 5A:
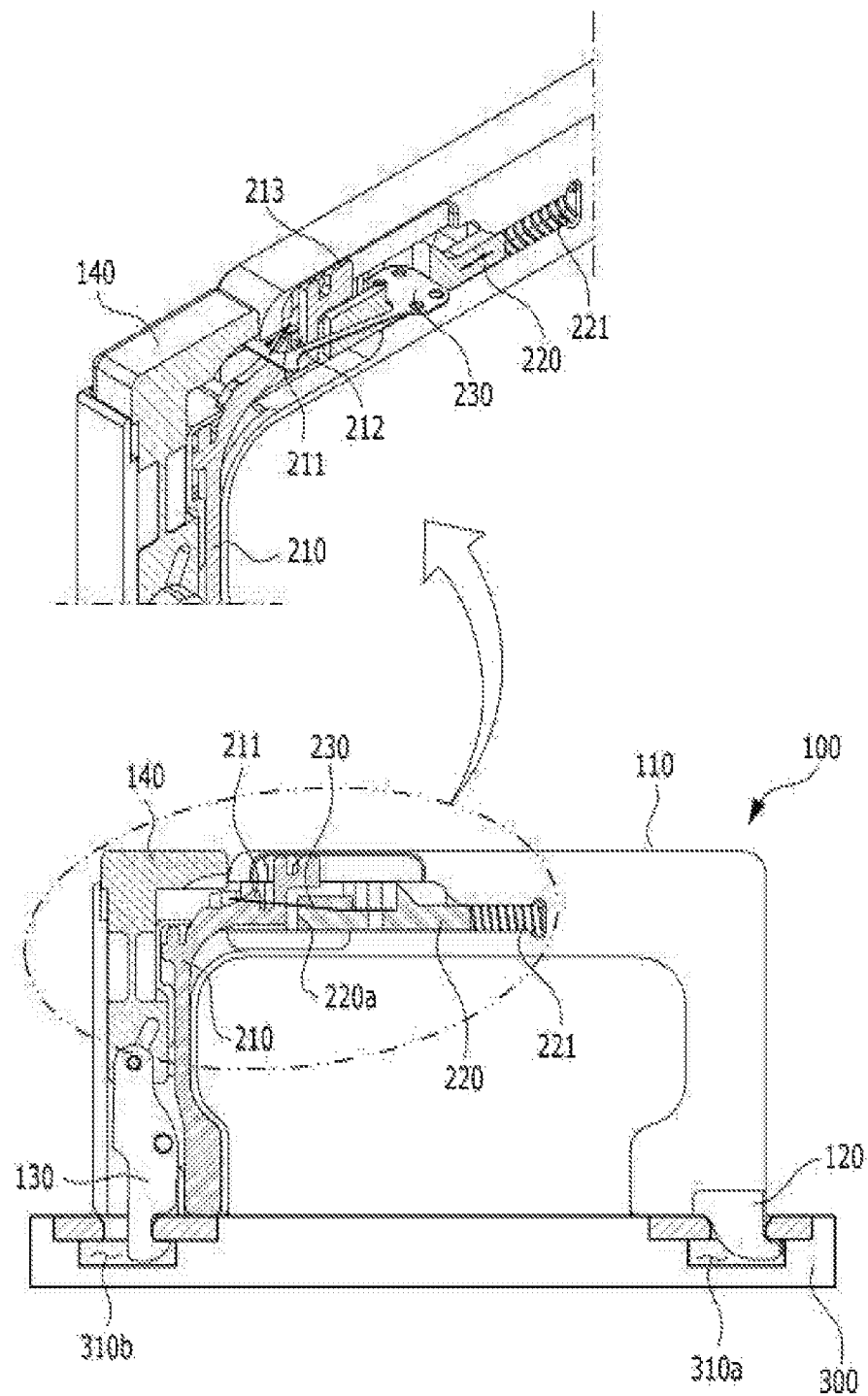
FIGS. 5A to 5D are sectional views showing a process wherein the handle according to the present invention is separated from the radiation detector body.
Figure 5B:
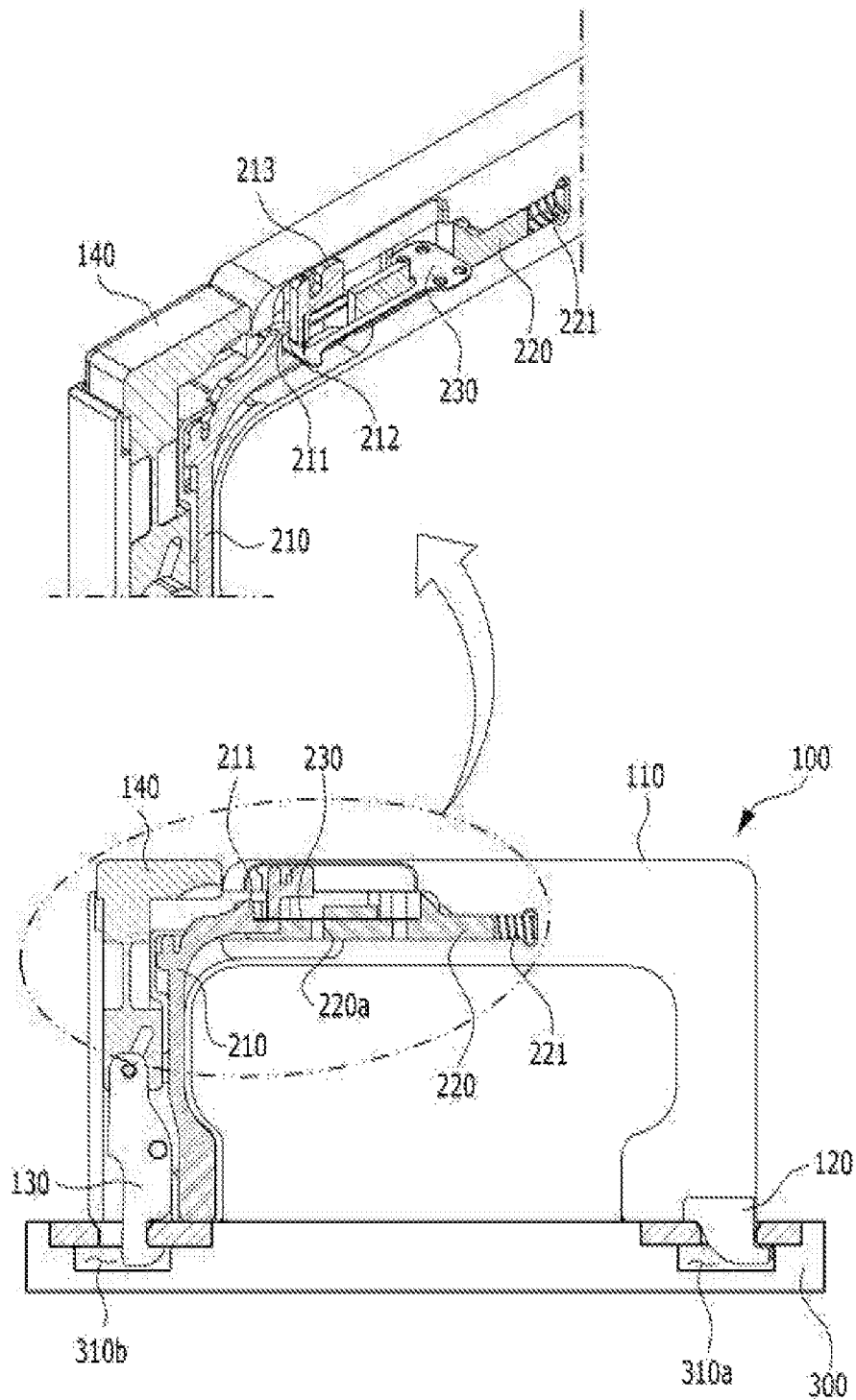
Figure 5C:
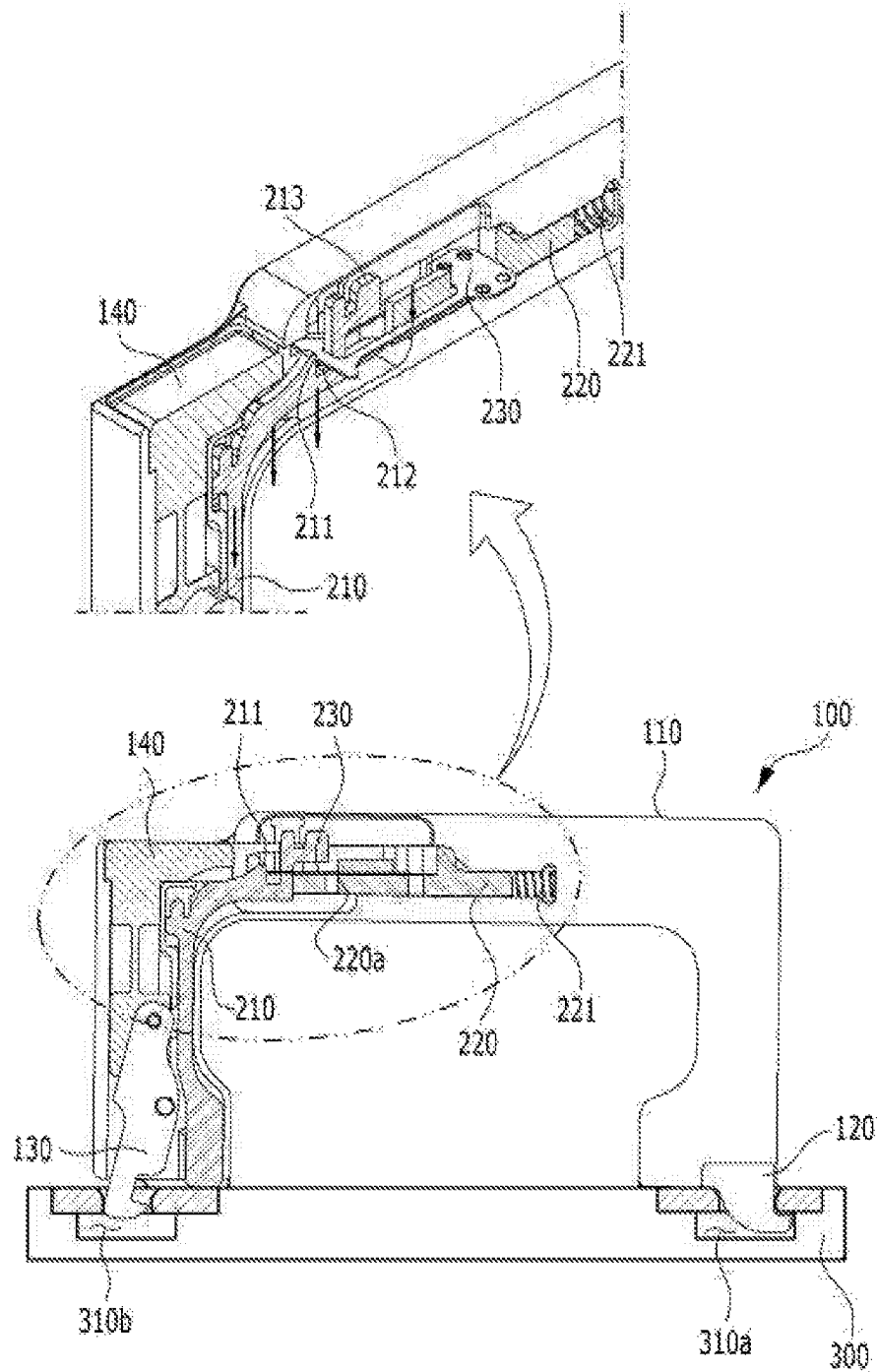
Figure 5D:
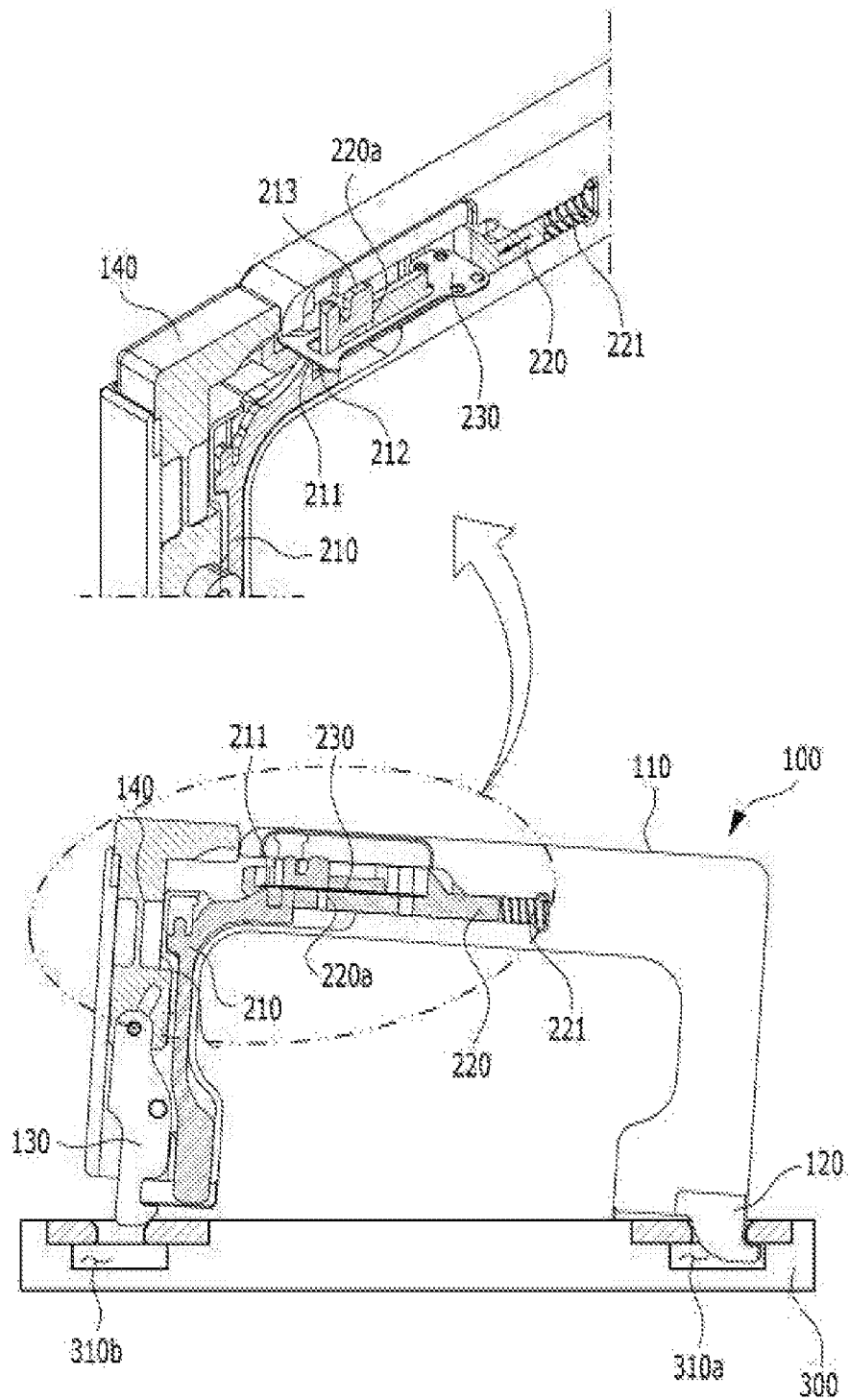

At this time, FIG. 5A is a sectional view showing a process wherein the moving member 220 moves backward by means of the user's manipulation for the manipulator 240, FIG. 5B is a sectional view showing a process wherein the stopper 230 is locked onto the locking groove 212 by means of the backward movement of the moving member 220 so that even if the moving member 220 and the protrusion portion 213 do not come into contact with each other, the forward movement of the moving member 220 is suppressed, FIG. 5C is a sectional view showing a process wherein the button member 140 is pressed by means of the user to separate the second hook 130 from the coupling groove 310b, and FIG. 5D is a sectional view showing a process wherein as the trigger 210 is descended by means of the separation of the second hook 130 from the coupling groove 310b, the stopper 230 escapes from the locking groove 212 to allow the double locking part 200 to return to its original state before the handle 100 is coupled to the radiation detector body 300.

In the state where the handle 100 is coupled to the radiation detector body 300, the moving member 220 moves forward so that the button member 140 cannot be pressed by the user, and so as to separate the handle 100 from the radiation detector body 300, accordingly, the manipulator 240 pushes backward by means of the user's manipulation to move the moving member 220 backward, as shown in FIG. 5A.

If the moving member 220 moves backward, the stopper 230 coupled to the moving member 220 also moves backward, and accordingly, the stopper 230 is bent upward by means of the curved surface portion 211, as shown in FIG. 5B, so that the stopper 230 is thus locked onto the locking groove 212 formed at the adjacent position to the curved surface portion 211.

As the stopper 230 is locked onto the locking groove 212, it cannot move forward even though the contact surface 220a of the moving member 220 comes into contact with the protrusion portion 213, and accordingly, the backward moving state of the moving member 220 is maintained to release the double locking state, so that the button member 140 can be pressed by the user.

In more detail, if the handle 100 is coupled to the radiation detector body 300, the front end of the moving member 220 is located on the underside of the button member 140, thereby achieving double locking for the handle 100. The moving member 220 moves backward by means of the user's manipulation to allow the stopper 230 coupled to the moving member 220 to be locked onto the locking groove 212 of the trigger 210, and even in the state where the trigger 210 is ascended, the backward moving state of the moving member 220 is maintained.

As the backward moving state of the moving member 220 is maintained, accordingly, the button member 140 is pressed only with the user's one hand, without any inconvenience occurring when the moving member 220 moves backward by the user's one hand and the button member 140 is pressed by his or her other hand so as to detach the handle 100 from the radiation detector body 300. As a result, the coupling state between the second hook 130 and the coupling groove 310b is released to detach the handle 100 from the radiation detector body 300.

Even though not shown in the drawings, a spring is disposed on the underside of the button member 140 to allow the descended button member 140 to be ascended again by means of the user's manipulation.

If the stopper 230 is locked onto the locking groove 212 to release the double locking, as shown in FIG. 5C, the button member 140 is pressed by the user to separate the second hook 130 from the coupling groove 310b, and if the second hook 130 is separated from the coupling groove 310b, as shown in FIG. 5D, the handle 100 is inclined to the direction of the first hook 120 to allow the trigger 210 ascended by the radiation detector body 300 to be descended again to its original state.

Even though not shown in the drawings, at this time, a spring is disposed on top of the trigger 210 to descend the ascended trigger 210 again by means of an elastic force thereof if the coupling state between the radiation detector body 300 and the lower end of the trigger 210 is released.

As the trigger 210 is descended, the stopper 230 locked onto the locking groove 212 escapes from the locking groove 212 to allow a portion of the fixed moving member 220 to move forward, and next, the moving member 220 while moving forward comes into contact with the protrusion portion 213 of the trigger 210 returned to its original state (in detail, the contact surface 220a of the moving member 220 comes into contact with one surface of the protrusion portion 213), so that the forward movement of the moving member 220 is suppressed to allow the handle 100 to be returned to its state before coupled to the radiation detector body 300. After that, if the first hook 120 coupled to the coupling groove 310a is separated, the handle 100 can be completely separated from the radiation detector body 300.

Next, an explanation on a radiation detector according to another embodiment of the present invention will be given with reference to FIGS. 2 and 3 and FIGS. 6A and 6B.

Figure 6A:
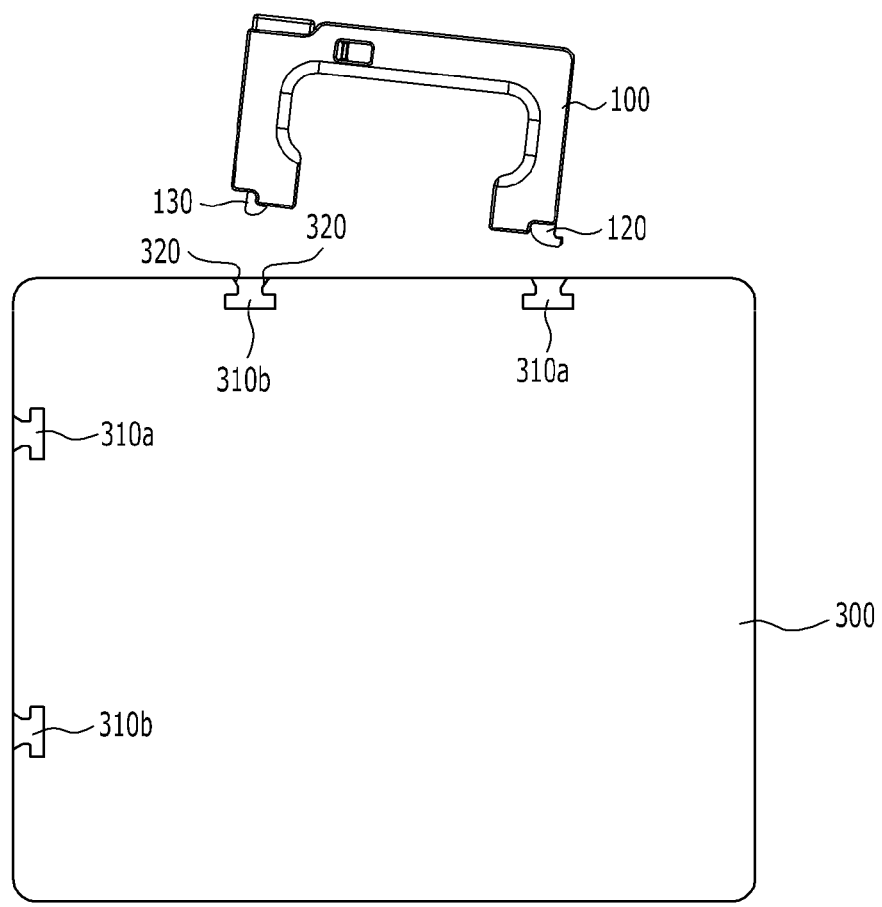
FIGS. 6A and 6B are front views showing a radiation detector according to another embodiment of the present invention, wherein a handle is attached to a radiation detector body, irrespective of its attaching direction.
Figure 6B:
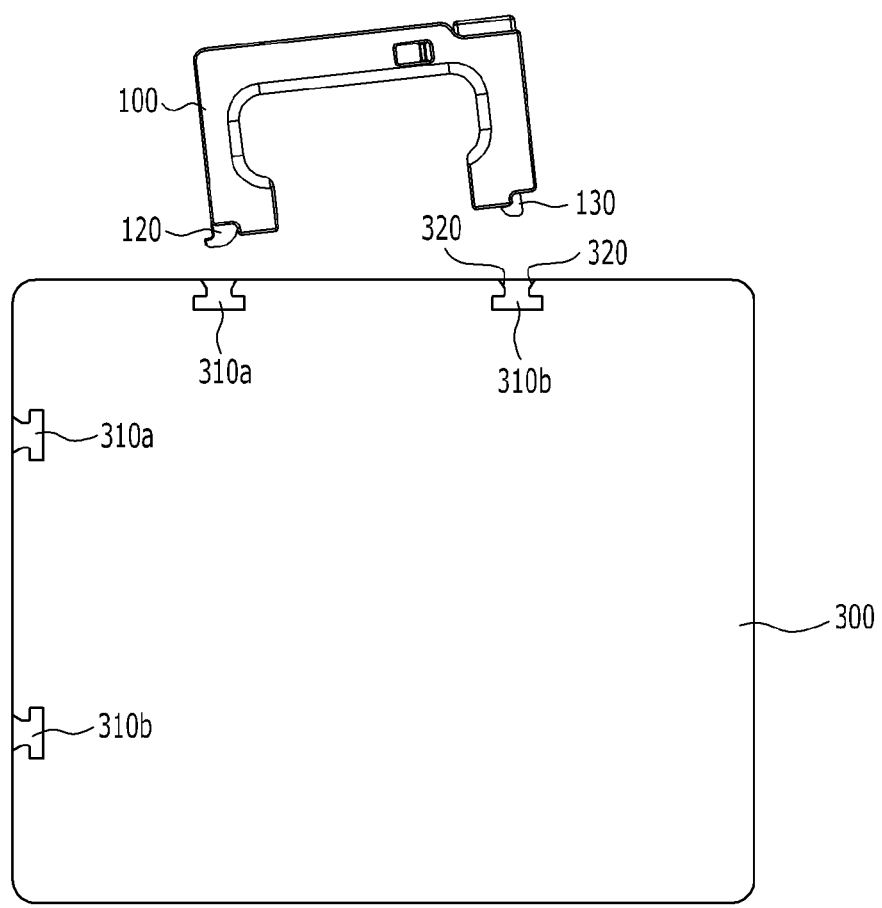

FIGS. 6A and 6B show a radiation detector according to another embodiment of the present invention, wherein a handle is attached to a radiation detector body, irrespective of its attaching direction.

The radiation detector according to another embodiment of the present invention includes: a radiation detector body 300 having a plurality of coupling grooves 310a and 310b formed on at least one or more surfaces thereof; and a handle 100 detachably coupled to the coupling grooves 310a and 310b.

As mentioned above, the handle 100 includes: a body 110 grasped by a user; a first hook 120 coupled to the coupling groove 310a or 310b; a button member 140 moving vertically according to the user's manipulation in such a manner as to release a coupling state of the handle 100; a second hook 130 engaging with the button member 140 and coupled to the coupling groove 310b or 310a; and a double locking part 200 including a trigger 210 disposed at the inside of the body 110 and moving vertically according to contact with the radiation detector body 300, a moving member 220 connected to the body 110 by means of a spring 221 and moving forward in a direction of the trigger 210 if the trigger 210 moves vertically, and a stopper 230 coupled to the moving member 220 in such a manner as to prevent the moving member 220 from moving forward if the handle 100 is detached from the radiation detector body 300.

However, the configuration of the handle 100 and the process of detachably coupling the handle 100 to the radiation detector body 300 are the same as above, and therefore, a detailed explanation on the handle 100 will be avoided for the brevity of the description.

The radiation detector body 300 has at least two or more coupling grooves 310a and 310b formed on one surface thereof, and the first hook 120 and the second hook 130 of the handle 100 are coupled to the coupling grooves 310a and 310b, so that the handle 100 is coupled to the radiation detector body 300.

At this time, as shown in FIGS. 6A and 6B, the coupling grooves 310a and 310b are formed on at least one or more surfaces of the square-shaped radiation detector body 300, and they are formed symmetrically on one surface of the radiation detector body 300, so that the first hook 120 and the second hook 130 are coupled to the coupling grooves 310a and 310b, irrespective of the positions of the coupling grooves 310a and 310b.

In more detail, as shown in FIG. 6A, the first hook 120 is first coupled to the coupling groove 310a formed on the right side, and after that, the second hook 130 is coupled to the coupling groove 310b formed on the left side, so that the handle 100 is coupled to the radiation detector body 300. Contrarily, as shown in FIG. 6B, the first hook 120 is first coupled to the coupling groove 310b formed on the left side, and after that, the second hook 130 is coupled to the coupling groove 310a formed on the right side, so that the handle 100 is coupled to the radiation detector body 300.

Further, slant surfaces 320 are formed on top ends of the coupling grooves 310a and 310b, and in a process where the second hook 130 is coupled to the coupling groove 310a or 310b, the second hook 130 comes into contact with the slant surface 320 and thus rotates in the opposite direction to the slant surface 320, so that the second hook 130 can be coupled gently to the coupling groove 310a or 310b.

Moreover, the coupling grooves 310a and 310b have sectional shapes of '⊥' when viewed on the side, and accordingly, the first hook 120 and the second hook 130 are coupled to the coupling grooves 310a and 310b, irrespective of their direction. Otherwise, the coupling groove 310a may have a sectional shape of '540' and the coupling groove 310b may have a sectional shape of '⌊'. Contrarily, the coupling groove 310a may have a sectional shape of '⌊', and the coupling groove 310b may have a sectional shape of '⌋'.

According to the sectional shapes of the coupling grooves 310a and 310b, at this time, the first hook 120 and the second hook 130 protrude outward from the handle 100, as shown in FIGS. 3 to 6B, and otherwise, if the coupling groove 310a has a sectional shape of '⌊' and the coupling groove 310b has a sectional shape of '⌋', the first hook 120 and the second hook 130 may protrude inward from the handle 100.

In conclusion, the handle for a radiation detector according to the present invention is configured to adopt such hook coupling and the double locking part, so that the handle can be coupled to the radiation detector body, irrespective of its attaching direction, thereby ensuring conveniences while being carried, and a gap between the radiation detector body and the handle is minimized through such hook coupling, thereby enhancing stability in their coupling, thereby solving the problems the conventional radiation detectors have had.

As described above, the handle for a radiation detector according to the present invention is configured to adopt hook coupling so that it can be coupled to the radiation detector body, irrespective of its attaching direction, thereby enabling fast detachable mounting.

Unlike the sliding coupling in the conventional radiation detector, in addition, the handle for a radiation detector according to the present invention is configured to adopt hook coupling to minimize a gap between the radiation detector body and the handle, thereby enhancing stability in their coupling and preventing the radiation detector body from falling down to the ground and being thus damaged.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

Further, terms used in this application are used to only describe specific exemplary embodiments and are not intended to restrict the present invention. An expression referencing a singular value additionally refers to a corresponding expression of the plural number, unless explicitly limited otherwise by the context.

It is therefore intended that the scope of the invention be limited not by this detailed description, but rather by the claims appended hereto, and also, it is to be understood that all technical ideas in the same range as above are within the scope of the invention.

What is claimed is:

1. A handle for a radiation detector, which is detachably mounted on a radiation detector body, comprising:
   a body configured to be grasped by a user;
   a first hook coupled to a coupling groove formed on the radiation detector body;
   a button member configured to move according to the user's manipulation in such a manner as to release a coupling state of the handle, the handle being coupled to the radiation detector body in the coupling state;
   a second hook engaging with the button member in such a manner as to be coupled to a coupling groove formed on the radiation detector body; and a double locking part disposed inside the body configured to be grasped by the user,
wherein the double locking part comprises:
a trigger moving vertically according to a contact with the radiation detector body;
a moving member connected to the body configured to be grasped by the user and moving forward in a direction of the trigger if the trigger moves vertically; and
a stopper coupled to the moving member in such a manner as to prevent the moving member from moving forward if the handle is detached from the radiation detector body.

2. The handle according to claim 1, wherein the trigger comprises:
a curved surface portion adapted to allow the stopper to be bent according to a horizontal movement of the moving member;
a locking groove adapted to fix the stopper thereto; and
a protrusion portion having one surface that comes into contact with the moving member to prevent the moving forward of the moving member.

3. The handle according to claim 2, wherein if the moving member moves backward to release the coupling state between the handle and the radiation detector body, the stopper is locked on the locking groove to prevent the moving member from moving forward.

4. The handle according to claim 3, wherein as the moving member moves backward, the button member can be pressed.

5. The handle according to claim 2, wherein if the button member is pressed in the coupling state where the handle is coupled to the radiation detector body, a coupling state between the second hook and the coupling groove of the radiation detector body is released to allow one side of the handle to be separated from the radiation detector body, and the trigger is descended, so that the stopper escapes from the locking groove to allow the moving member to move forward until coming into contact with the protrusion portion.

6. The handle according to claim 1, wherein the moving member further comprises a manipulator exposed on an outer surface of the body configured to be grasped by the user, the manipulator being configured in such a manner as to move the moving member forward or backward in response to manipulation.

7. The handle according to claim 1, wherein if the first hook and the second hook are coupled to the coupling grooves of the radiation detector body, the trigger is ascended, so that the moving member moves forward to prevent the button member from being pressed.

8. A radiation detector comprising:
a radiation detector body having a plurality of coupling grooves formed on at least one or more surfaces thereof; and
a handle detachably coupled to the coupling grooves, wherein the handle comprises:
a body configured to be grasped by a user;
a first hook coupled to a coupling groove on one side;
a button member configured to move vertically according to the user's manipulation in such a manner as to release a coupling state of the handle;
a second hook engaging with the button member and coupled to a coupling groove on another side; and
a double locking part having a trigger disposed inside of the body configured to be grasped by the user and moving vertically according to a contact with the radiation detector body, a moving member connected to the body configured to be grasped by the user by means of a spring and moving forward in a direction of the trigger if the trigger moves vertically, and a stopper coupled to the moving member in such a manner as to prevent the moving member from moving forward if the handle is detached from the radiation detector body.

9. The radiation detector according to claim 8, wherein the coupling grooves are formed symmetrically on at least one or more of the surfaces of the radiation detector body.

* * * * *